United States Patent [19]

Donzis

[11] Patent Number: 4,891,220

[45] Date of Patent: Jan. 2, 1990

[54] METHOD AND COMPOSITION FOR TREATING HYPERLIPIDEMIA

[75] Inventor: Byron A. Donzis, Houston, Tex.

[73] Assignee: ImmuDyne, Inc., Palo Alto, Calif.

[21] Appl. No.: 219,336

[22] Filed: Jul. 14, 1988

[51] Int. Cl.$^4$ .............................................. A61K 35/72
[52] U.S. Cl. ....................................... 424/88; 424/95; 424/195.1; 514/356; 514/571
[58] Field of Search .................... 424/95; 514/356, 571

[56] References Cited

U.S. PATENT DOCUMENTS 3,081,226  3/1963  DiLuzio ............................. 514/61
3,709,991  1/1973  Miller ................................ 514/356
4,138,479  2/1979  Truscheit et al. .................. 514/885

OTHER PUBLICATIONS

Leja, D.; Stuce, M.; Liepa, V.; Bass-Shadkhan, Kh.; Klavina, Z.; Burmeister, M.; and Preimate, E., Biochemical Indexes in Rabbits with Alimentary Atherosclerosis During Administration of Zymosan, CA 76(17): 94588.

The Merck Index, 10th ed., Merck & Co., Inc., Rahway, N.J., 1983, #4246.

Z. Holan et al., *Folia Microbiol* (1980) 25:501–04.

*Primary Examiner*—Amelia Burgess Yarbrough
*Assistant Examiner*—Jean C. Witz
*Attorney, Agent, or Firm*—Irell & Manella

[57] ABSTRACT

Serum levels of cholesterol are improved by administration of yeast cell wall extract LCP-100 Series ™ product LR323 ™ in combination with a cholesterol regulating agent, preferably niacin or gemfibrozil.

16 Claims, No Drawings

METHOD AND COMPOSITION FOR TREATING HYPERLIPIDEMIA

DESCRIPTION

1. Technical Field

This invention relates to methods and compositions for lower serum lipid levels. More specifically, it relates to compositions comprising soluble yeast cell wall fractions in combination with cholesterol regulating agents, for treatment of elevated serum lipids.

2. Background of the Invention

Transportation and storage of cholesterol and other lipids in the bloodstream is effected by a family of proteins including high-density lipoprotein (HDL), low-density lipoprotein (LDL), and very low-density lipoprotein (VLDL). A number of pathological states, including atherosclerosis, are associated with imbalance between the concentrations of these lipoproteins. In general, an increased ratio of LDL and VVLDL to HDL is correlated with an increased incidence of cardiovascular disease.

There are several therapeutic agents available which may adjust the ratio of LDL-VLDL to HDL. For example, colestipol hydrochloride (U.S. Pat. Nos. 3,692,895 and 3,803,237) is a basic anion exchange resin which, when ingested, sequesters bile acids in the intestine. This stimulates the production of bile acids, which uses and depletes the body's stored cholesterol. This in turn reduces LDL levels, and elevates HDL levels. VLDL is not affected. However, colestipol hydrochloride has numerous side effects due to its mechanism of action: because it binds bile acids, it interferes with the absorption of lipid-soluble nutrients and drugs, for example fat-soluble vitamins (A, D, and K). It also tends to cause constipation (bile acids normally stimulate the intestinal mucosa), and may exacerbate diverticulitis.

The compound 4-aminosalicylic acid and its calcium and sodium salts, is sometimes used for treatment of familial hypercholesterolemia. At dosages of 6–8 g/day in adults, it may lower LDL levels by 15–20%, and may lower VLDL levels by 25%. However, it is also known to cause gastrointestinal disturbances.

Gemfibrozil (Lopid®), 5-(2,5-dimethylphenoxy)-2,2-dimethylpentanoic acid, is also used in such treatment. Gemfibrozil inhibits synthesis of VLDL and VLDL carrier apolipoprotein, and to some extent the synthesis of LDL, while increasing levels of HDL. Gemfibrozil is described in U.S. Pat. No. 3,674,836.

Probucol, 2,2-di(3,5-di-t-butyl-4-hydroxyphenylthio)propane (Lorelco®), inhibits cholesterol synthesis, and lowers plasma LDL (J. Med. Chem., (1972) 13:722). Reductions of about 9–16% in plasma cholesterol content are typical after three months of treatment (500 mg bid).

Niacin (3-pyridinecarboxylic acid) is also administered for hypercholesterolemia, at a dosage of about 1.5 to 6 g/day orally. Other pharmaceutical agents occasionally administered for hyperlipidemia include neomycin, norethindrone acetate, oxandrolone, and dextrothyroxine (Remington's Pharmaceutical Sciences, (17th Ed., Mack Pub. Co., 1985), pp. 863–865).

Di Luzio, U.S. Pat. No. 3,081,226 discloses zymosan, an extract prepared from yeast as described by Pillemer et al., J. Biol. Chem. (1941) 137:139. Di Luzio disclosed that zymosan did not affect lipid levels in animals fed a cholesterol-free diet, but did reduce cholesterol levels in animals fed an atherogenic diet. In responding animals, the Kupffer cells were found to be hyperplastic. Di Luzio then found that zymosan at 0.4 mg/Kg in aqueous Tween®-80, Residue A (zymosan after chloroform extraction) at 0.1 mg/Kg, Residue B (Residue A after acid hydrolysis) at 0.1 mg/Kg, and yeast cell wall glucan at 0.1 mg/Kg administered to rats iv induced Kupffer cell hyperplasia.

Certain water-soluble extracts obtained from yeast cell wall preparations were described by Truscheit et al, U.S. Pat. No. 4,138,479. This product, available as LCP-100 Series ™, product LR323 ™ is disclosed to be an immunomodulator. It presumably functions by stimulating the reticuloendothelial system.

DISCLOSURE OF THE INVENTION

I have now discovered that combinations of LCP-100 Series ™ product LR323 ™ and cholesterol regulating agents, preferably niacin or gemfibrozil, are more effective at lowering serum cholesterol than LCP-100 Series ™ product LR323 ™ or the cholesterol regulating agent individually. Thus, one aspect of the invention relates to methods for treating lipid-associated cardiovascular disorders by administering an effective amount of LCP-100 Series ™ product LR323 ™ and cholesterol regulating agent, preferably niacin or gemfibrozil. Another aspect of the invention relates to compositions useful in such treatment, i.e., compositions containing an effective amount of LCP-100 Series ™ product LR323 ™ and a cholesterol regulating agent, especially niacin or gemfibrozil.

MODES OF CARRYING OUT THE INVENTION

A. Definitions

As used herein, the term "lipid-associated cardiovascular disorders" includes those pathological states correlated with abnormal lipid metabolism, transport, and/or storage. Examples of such states include, but are not limited to, atherosclerosis, hyperlipidemia, hypercholesterolemia, and the like. These diseases are characterized by elevated levels of cholesterol and other lipids, and by elevated ratios of LDL to HDL.

The term "cholesterol regulating agent" refers to pharmaceutical agents useful for lowering serum lipid levels and/or regulating the ratio of HDL/LDL in serum. Exemplary cholesterol regulating agents include, without limitation, 4-aminosalicylic acid, niacin, gemfibrozil, probucol, neomycin, norethindrone acetate, oxandrolone, dextrothyroxine, and the like. Presently preferred cholesterol regulating agents are niacin and gemfibrozil.

The term "niacin" refers to 3-pyridinecarboxylic acid, and to equivalent compounds which are converted to 3-pyridinecarboxylic acid in vivo.

The term "gemfibrozil" refers to 5-(2,5-dimethylphenoxy)-2,2-dimethylpentanoic acid, and its pharmaceutically acceptable salts and esters. Gemfibrozil is commercially available under the trademark Lopid®, and may be prepared by the methods disclosed in U.S. Pat. No. 3,674,836, incorporated herein by reference.

The term "LCP-100 Series ™ product LR323 ™" refers to the water-soluble yeast cell wall extract described in U.S. Pat. No. 4,138,479 (Example 1A), incorporated herein by reference. LCP-100 Series ™ product LR323 ™ may be prepared by the methods taught therein, or may be purchased commercially from ImmunDyne, Inc. (Palo Alto, CA).

The term "treatment" as used herein refers to any of (i) the prevention of disease (prophylaxis), (ii) the reduction or elimination of symptoms, and (iii) the complete remission of the disease in patients where it has been diagnosed. In the instant case, treatment relates to prevention of a lipid-associated cardiovascular disorder in a subject at risk for such a disorder but not yet diagnosed as having such, to reduction of symptoms of a lipid-associated cardiovascular disorder (e.g., formation of atherosclerotic plaques), and to elimination of the disease (e.g., return of serum cholesterol levels to normal).

The term "effective amount" as used herein refers to the amount of LCP-100 Series ™ product LR323 ™ or cholesterol regulating agent needed to effect treatment of a lipid-associated cardiovascular disease. The precise amount of these compounds required will vary with the particular compounds or derivatives employed, the age and condition of the subject to be treated, and the nature and severity of the condition. However, the effective amount may be determined by one of ordinary skill in the art with only routine experimentation, following methods known in the art In general, for lowering serum LDL and cholesterol levels, an amount of LCP-100 Series ™ product LR323 ™ (when used with niacin or gemfibrozil) of about 0.001 to about 5.0 mg/Kg/day is sufficient, preferably about 0.01 to 1.0 mg/Kg/day, and most preferably about 0.1 mg/Kg/day. An amount of niacin between about 5.0 and about 150 mg/Kg/day is adequate, preferably about 10–40 mg/Kg/day, and most preferably about 20–25 mg/Kg/day. Gemfibrozil is administered at a rate of about 5.0 to 180 mg/Kg/day, preferably about 10–40 mg/Kg/day, most preferably about 20 mg/Kg/day. Cholesterol regulating agents, including both niacin and gemfibrozil, have known side effects at high dosages: the occurrence and severity of these side effects will as a practical matter determine the effective upper limit for dosage administered. However, in the practice of the invention, it is unlikely that any side effects will be experienced at the preferred dose levels.

The term "pharmaceutically acceptable carrier" refers to any generally acceptable excipient that is relatively inert, non-toxic, and non-irritating. As the compositions of the invention are well suited to oral administration, preferred carriers will facilitate formulation in tablet or capsule form. Exemplary carriers include calcium carbonate, sucrose, dextrose, mannose, albumin, starch, cellulose, silica gel, polyethylene glycol (PEG), dried skim milk, rice flour, magnesium stearate, and the like. Carriers for parenteral administration include, without limitation, aqueous solutions of dextrose, saline, pure water, ethanol, glycerol, propylene glycol, peanut oil, sesame oil, polyoxyethylene-polyoxypropylene block polymers, and the like. Suitable formulations and additional carriers are described in Remington's Pharmaceutical Sciences, (17th Ed., Mack Pub. Co., 1985).

B. General Method

LCP-100 Series ™ product LR323 ™ is prepared by the method disclosed in U.S. Pat. No. 4,138,479 (Example 1A). Generally, a yeast culture is grown under sterile conditions, and is centrifuged to provide a yeast sediment. The sediment is then suspended in buffered $Na_2HPO_4$ and heated at 100° C. at pH 8.9 to effect sterilization. The sediment is then treated with toluene and trypsin for 16 days to proteolyze the yeast. The product is then suspended in cold water and toluene, centrifuged at 19,000 rpm, heated at 90° C. for one hour, centrifuged again, suspended in absolute ethanol, filtered, and vacuum dried to provide zymosan. The zymosan is suspended in distilled water, and an equal volume of 90% aqueous phenol is added. The mixture is heated to 68° C., cooled, and the resulting emulsion centrifuged. The aqueous phase is removed and retained. The remaining phases (solid and phenol) are heated to 68° C. with an additional volume of cold water, cooled, and centrifuged again. The aqueous phase is combined with the retained aqueous phase, and the solution dialyzed against distilled water. The retentate is reduced under reduced pressure (35°–40° C.) to 10% of its initial volume, the resulting precipitate removed by centrifugation and discarded, and the aqueous supernatant lyophilized to provide LCP-100 Series ™ product LR323 ™.

Niacin, gemfibrozil, and other cholesterol regulating agents are obtained from commercial sources, or prepared by methods generally known in the art.

The compositions of the invention may be formulated using techniques standard in the art. As the active agents in the preferred compositions comprise about 20 mg/Kg/day, or about 1.4 g/day for a typical 70 Kg adult, the compositions are preferably administered in several capsules taken bid, tid, or qid, or are administered in a liquid syrup or elixir.

C. Examples

The examples presented below are provided as a further guide to the practitioner of ordinary skill in the art, and are not to be construed as limiting the invention in any way.

EXAMPLE 1

(Formulations of the Invention)

(A) A representative capsule formulation is prepared as follows:

| | |
|---|---|
| LCP-100 | 0.1 mg |
| Niacin | 20.0 mg |
| starch | 0.30 mg |
| magnesium stearate | 0.30 mg |
| lactose | 11.6 mg |
| polyvinylpyrrolidone | 0.30 mg |

The niacin, starch, magnesium stearate, lactose, and polyvinylpyrrolidone are granulated in methanol, dried, and mixed with the LCP-100 Series ™ product LR323 ™. The resulting mixture is then loaded into capsules. Alternatively, the mixture may be tableted by standard methods.

(B) Another capsule formulation is prepared as follows:

| | |
|---|---|
| LCP-100 | 0.1 mg |
| gemfibrozil | 20.0 mg |
| starch | 0.30 mg |
| magnesium stearate | 0.30 mg |
| lactose | 11.6 mg |
| polyvinylpyrrolidone | 0.30 mg |

The gemfibrozil, starch, magnesium stearate, lactose, and polyvinylpyrrolidone are granulated in methanol, dried, and mixed with the LCP-100 Series ™ product LR323 ™. The resulting mixture is then loaded into capsules. Alternatively, the mixture may be tableted by standard methods.

(C) An oral suspension is prepared as follows:

| | |
|---|---|
| LCP-100 | 2.0 mg |
| niacin (or gemfibrozil) | 400.0 mg |
| fumaric acid | 0.5 g |
| NaCl | 2.0 g |
| methyl paraben | 0.1 g |
| granulated sugar | 25.5 g |
| sorbitol (70% aq) | 12.85 g |
| Veegum K | 1.0 g |
| flavorings | 0.035 mL |
| colorings | 0.5 mg |
| distilled water qs | 100.0 mL |

The components are mixed together and stored in a sealed vessel, to provide 20×5 mL doses.

(D) A formulation suitable for parenteral administration is prepared as follows:

| | |
|---|---|
| LCP-100 | 2.0 mg |
| niacin (or gemfibrozil) | 400.0 mg |
| $KH_2PO_4$ buffer (0.4M) | 2.0 mL |
| KOH (1N) qs | pH 7.0 |
| water qs | 20.0 mL |

The components are mixed together to provide 20 doses of 1 mL.

EXAMPLE 2

(Comparison of Individual Agents)

Niacin, gemfibrozil, and LCP-100 Series ™ product LR323 ™ were compared individually for efficacy in lowering serum cholesterol levels.

Niacin and gemfibrozil were evaluated at dose levels of 10, 30, 100, and 300 mg/Kg/day. LCP-100 Series ™ product LR323 ™ was administered at a dose level of 1.0 mg/Kg/day. Doses were formulated in 0.5 mL volumes as aqueous suspensions and as 2% Tween ® 80 solutions for oral administration.

Male Sprague-Dawley rats, 5–6 weeks old, weighing 160–180 grams were divided into experimental groups of 10 animals per group. A dose of one of the formulations was administered to each animal for seven consecutive days, at approximately the same time (e.g., 8:00 a.m.) each day. Food and water were available ad libitum for the duration of the study except that food was withdrawn after the final dose on day 7 and animals were fasted for 24 hours. At the end of that period, animals were anesthetized with $CO_2$ and blood samples drawn from the orbital sinus of each rat. After centrifuging, serum samples from each animal were harvested and assayed for total cholesterol, HDL, and serum triglycerides. LDL was calculated as the difference between the total cholesterol and HDL.

The results are presented in Table 1.

TABLE 1

| Group | Total* | LDL* | HDL* | % LDL |
|---|---|---|---|---|
| Control | 55.0 | 18.0 | 37.0 | 32.7 |
| niacin[1] | 62.0 | 15.0 | 47.0 | 24.2 |
| gemfibrozil[1] | 88.0 | 17.0 | 71.0 | 19.3 |
| LCP-100[2] | 58.0 | 13.0 | 45.0 | 22.4 |

[1]dosage 300 mg/Kg/day
[2]dosage 1.0 mg/Kg/day
*data in mg/dL serum for total cholesterol, LDL concentration, and HDL concentration Total cholesterol values for niacin and LCP-100 Series ™ product LR323 ™ were essentially the same as those for the vehicle controls. Gemfibrozil actually elevated total cholesterol. While a reduction in total cholesterol is desirable, a lowering of the LDL fraction is considered more desirable. HDL cholesterol is thought to represent material destined for transport to the liver for disposal. From the standpoint of LDL reduction, all three compounds were shown to be active. LCP-100 Series ™ product LR323 ™ exhibited an effect intermediate to niacin and gemfibrozil. These results are extrapolated to humans by reducing the dose in mg/Kg by a factor of 10.

EXAMPLE 3

(Combination Therapy)

Treatment of rats as in Example 2 above was carried out using niacin or gemfibrozil at dosages of 200 mg/Kg/day with and without 1.0 mg/Kg/day of LCP-100 Series ™ product LR323 ™.

Treatment groups were as follows:

(1) vehicle (control)
(2) 200 mg/Kg/day gemfibrozil in one dose
(3) 200 mg/Kg/day divided into two doses (bid)
(4) 200 mg/Kg/day gemfibrozil, 1.0 mg/Kg/day LCP-100 Series ™ product LR323 ™
(5) 200 mg/Kg/day gemfibrozil, 1.0 mg/Kg/day LCP-100 Series ™ product LR323 ™ bid
(6) 1.0 mg/Kg/day LCP-100 Series ™ product LR323 ™
(7) 200 mg/Kg/day niacin
(8) 200 mg/Kg/day niacin bid
(9) 200 mg/Kg/day niacin, 1.0 mg/Kg/day LCP-100 Series ™ product LR323 ™
(10) 200 mg/Kg/day gemfibrozil, 1.0 mg/Kg/day LCP-100 Series ™ product LR323 ™ bid The treatment groups were dosed for 5 consecutive days (instead of 7 as in Example 2). All rats were bled 3 hours after dosing on day 5 and serum samples prepared and analyzed as in Example 2. These samples are denoted as "fed" data. All rats were then fasted overnight and bled in the morning of day 6 (7:00 a.m.). This data is denoted as "fasted". The results are presented in Table 2 below.

TABLE 2

| | Group | Trig* | Total+ | HDL+ | LDL+ | % LDL |
|---|---|---|---|---|---|---|
| 1 | Control (fed) | 86 | 79 | 55 | 24 | 30.4 |
|   | fasted | 77 | 73 | 49 | 24 | 32.9 |
| 2 | gemfibrozil | 41 | 67 | 46 | 21 | 31.3 |
|   | (fed) fasted | 84 | 89 | 60 | 29 | 32.6 |
| 3 | gemf bid | 40 | 59 | 43 | 16 | 27.1 |
|   | (fed) fasted | 96 | 90 | 63 | 27 | 30.0 |
| 4 | gemf + LCP | 40 | 60 | 43 | 17 | 28.3 |
|   | (fed) fasted | 82 | 90 | 60 | 30 | 33.3 |
| 5 | gemf/LCP | 44 | 60 | 41 | 19 | 31.7 |
|   | bid (fed) fasted | 97 | 90 | 58 | 32 | 35.6 |
| 6 | LCP-100 | 77 | 70 | 45 | 25 | 35.7 |
|   | (fed) fasted | 95 | 70 | 42 | 28 | 40.0 |
| 7 | niacin (fed) | 48 | 76 | 54 | 22 | 28.9 |
|   | fasted | 122 | 76 | 50 | 26 | 34.2 |
| 8 | niacin bid | 48 | 62 | 46 | 16 | 25.8 |
|   | (fed) fasted | 132 | 61 | 41 | 20 | 32.8 |
| 9 | niacin + LCP (fed) fasted | 45 129 | 62 67 | 54 44 | 8 23 | 12.9 34.3 |
| 10 | niacin/LCP bid (fed) fasted | 46 120 | 52 57 | 40 34 | 12 23 | 23.1 40.4 |

*serum triglycerides, mg/dL serum
+data in mg/dL serum for total cholesterol, LDL concentration, and HDL concentration Again with respect to LDL reduction, LCP-100 Series ™ product LR323 ™, while ineffective alone, enhanced the activity of both known lipid regulators when administered as a combination in a single dose.

The effect with niacin is particularly striking. These results are extrapolated to humans by reducing the dose in mg/Kg by a factor of 10.

What is claimed is:

1. A composition for treating lipid-associated cardiovascular disorders in a mammal, which composition comprises:
    an effective amount of a water soluble yeast cell wall extract, obtained by subjecting disrupted yeast cell wall material to extraction with from 10 to 100 times the amount by volume of a mixture of substantially equal amounts of water and phenol, and separating and dialyzing the aqueous phase to remove any low molecular weight sugars, amino acids, peptides, lipids and yeast metabolites, and isolating said extract from the dialysis retentate; and
    an effective amount of a cholesterol regulating agent selected from the group consisting of gemfibrozil and niacin.

2. The composition of claim 1 wherein said cholesterol regulating agent is niacin.

3. The composition of claim 1 wherein said cholesterol regulating agent is gemfibrozil.

4. A pharmaceutical formulation for treating lipid-associated cardiovascular disorders in a mammal, which formulation comprises:
    an effective amount of a water soluble yeast cell wall extract, obtained by subjecting disrupted yeast cell wall material to extraction with from 10 to 100 times the amount by volume of a mixture of substantially equal amounts of water and phenol, and separating and dialyzing the aqueous phase to remove any low molecular weight sugars, amino acids, peptides, lipids and yeast metabolites, and isolating said extract from the dialysis retentate;
    an effective amount of a cholesterol regulating agent selected from the group consisting of gemfibrozil and niacin; and
    a pharmaceutically acceptable carrier.

5. The formulation of claim 4, wherein said cholesterol regulating agent is gemfibrozil.

6. The formulation of claim 4 wherein said cholesterol regulating agent is niacin.

7. The formulation of claim 6 wherein said niacin and said water soluble yeast cell wall extract are present in a ratio of about 5:1 to about 1500:1.

8. The formulation of claim 7 wherein said niacin and said water soluble yeast cell wall extract are present in a ratio of about 75:1 to about 500:1.

9. The formulation of claim 5 wherein said gemfibrozil and said water soluble yeast cell wall extract are present in a ratio of about 5:1 to about 1500:1.

10. The formulation of claim 9 wherein said gemfibrozil and said water soluble yeast cell wall extract are present in a ratio of about 75:1 to about 500:1.

11. A method for treating lipid-associated cardiovascular disorders, which method comprises:
    administering to a mammal an effective amount of a water soluble yeast cell wall extract in combination with an effective amount of a cholesterol regulating agent selected from the group consisting of gemfibrozil and niacin, wherein said water soluble yeast cell wall extract is obtained by subjecting disrupted yeast cell wall material to extraction with from 10 to 100 times the amount by volume of a mixture of substantially equal amounts of water and phenol, and separating and dialyzing the aqueous phase to remove any low molecular weight sugars, amino acids, peptides, lipids and yeast metabolites, and isolating said extract from the dialysis retentate.

12. The method of claim 11 wherein said water soluble yeast cell wall extract is administered in an amount of about 0.001 to about 1.0 mg/Kg/day.

13. The method of claim 12 wherein said cholesterol regulating agent comprises niacin administered in an amount of about 5.0 to about 150 mg/Kg/day.

14. The method of claim 13 wherein the niacin is administered in an amount of about 10–30 mg/Kg/day.

15. The method of claim 12 wherein said cholesterol regulating agent is gemfibrozil administered in an amount of about 5.0 to 180 mg/Kg/day.

16. The method of claim 15 wherein the gemfibrozil is administered in an amount of about 10–30 mg/Kg/day.

* * * * *